United States Patent
Elmaanaoui

(10) Patent No.: US 11,145,054 B2
(45) Date of Patent: Oct. 12, 2021

(54) METHODS AND SYSTEMS FOR DISPLAYING INTRALUMINAL IMAGES

(71) Applicant: Canon U.S.A., Inc., Melville, NY (US)

(72) Inventor: Badr Elmaanaoui, Belmont, MA (US)

(73) Assignee: Canon U.S.A., Inc., Melville, NY (US)

( * ) Notice: Subject to any disclaimer, the term of this patent is extended or adjusted under 35 U.S.C. 154(b) by 26 days.

(21) Appl. No.: 16/460,864

(22) Filed: Jul. 2, 2019

(65) Prior Publication Data

US 2020/0013164 A1    Jan. 9, 2020

Related U.S. Application Data

(60) Provisional application No. 62/695,380, filed on Jul. 9, 2018.

(51) Int. Cl.
| | | |
|---|---|---|
| *A61B 1/00* | (2006.01) |
| *A61B 1/04* | (2006.01) |
| *A61B 5/00* | (2006.01) |
| *G06T 3/00* | (2006.01) |
| *G06T 7/00* | (2017.01) |
| *G06T 7/33* | (2017.01) |
| *G16H 30/40* | (2018.01) |

(52) U.S. Cl.
CPC ........ *G06T 7/0012* (2013.01); *A61B 1/00009* (2013.01); *A61B 1/04* (2013.01); *G06T 7/33* (2017.01); *A61B 5/6852* (2013.01); *G06T 2207/10068* (2013.01); *G06T 2207/10132* (2013.01); *G06T 2207/30101* (2013.01); *G16H 30/40* (2018.01)

(58) Field of Classification Search
None
See application file for complete search history.

(56) References Cited

U.S. PATENT DOCUMENTS

| | | | |
|---|---|---|---|
| 9,292,918 B2 | 3/2016 | Zagrodsky et al. | |
| 10,376,236 B2* | 8/2019 | Abe | ........................ G06T 7/246 |
| 2004/0019253 A1 | 1/2004 | Tsujita et al. | |
| 2010/0094127 A1* | 4/2010 | Xu | ........................ A61B 5/7425 |
| | | | 600/425 |
| 2011/0033098 A1 | 2/2011 | Richter et al. | |
| 2011/0071404 A1 | 3/2011 | Schmitt | |
| 2012/0323311 A1* | 12/2012 | McClain | ................. A61L 31/16 |
| | | | 623/1.42 |
| 2013/0165753 A1 | 6/2013 | Takahashi | |

(Continued)

FOREIGN PATENT DOCUMENTS

| | | |
|---|---|---|
| JP | 2005028123 A | 2/2005 |
| JP | 2014237021 A | 12/2014 |

(Continued)

OTHER PUBLICATIONS

Wang, "Heartbeat Optical Coherence Tomography," PhD Thesis, Erasmus University Rotterdam, Mar. 2015 (Year: 2015).*

(Continued)

*Primary Examiner* — Soo Shin
(74) *Attorney, Agent, or Firm* — Canon U.S.A., Inc., IP Division

(57) ABSTRACT

Methods and systems for imaging a lumen, wherein imaging is manipulated to provide centered magnified version of the image, yielding precise and centered images for better efficacy in real-time treatment by practitioners and experts.

20 Claims, 7 Drawing Sheets

(56) References Cited

U.S. PATENT DOCUMENTS

| | | | |
|---|---|---|---|
| 2014/0193057 A1* | 7/2014 | Zagrodsky | G06T 7/0014 |
| | | | 382/131 |
| 2019/0125361 A1* | 5/2019 | Shelton, IV | A61B 17/07207 |
| 2019/0374109 A1* | 12/2019 | Wu | G06T 7/12 |
| 2020/0013164 A1* | 1/2020 | Elmaanaoui | G06T 3/00 |

FOREIGN PATENT DOCUMENTS

| | | |
|---|---|---|
| JP | 2016516466 A | 6/2016 |
| WO | 2016/104368 A1 | 6/2016 |

OTHER PUBLICATIONS

Rob Reilink,Image-Based Flexible Endoscope Steering, The 2010 IEEE/RSJ International Conference on Intelligent Robots and Systems, Oct. 18-22, 2010, pp. 2339-2344, Taipei, Taiwan.
Optis Integrated System Instructions for Use, Instruction Manual, St. Jude Medical, Inc.,Apr. 2014. pp. 1-248, US.
Ilumien Optis System Instructions for Use, Instruction Manual, St. Jude Medical, Inc., Mar. 2013, pp. 1-220, US.

* cited by examiner

METHODS AND SYSTEMS FOR DISPLAYING INTRALUMINAL IMAGES

CROSS REFERENCE TO RELATED PATENT APPLICATIONS

This application claims priority to U.S. Provisional Patent Application No. 62/695,380 filed on Jul. 9, 2018, in the United States Patent and Trademark Office, the disclosure of which is incorporated herein in its entirety by reference.

FIELD OF THE DISCLOSURE

The present disclosure relates generally to methods and systems for imaging a cross-section of a lumen. More particularly, the present disclosure is directed toward methods and systems for displaying real-time images of a lumen with high accuracy at a high magnification level. In addition, the subject disclosure is relevant in evaluating and diagnosing biological objects, such as, but not limited to, gastrointestinal, pulmonary and/or intravascular applications, which may be obtained via one or more instruments, such as, but not limited to, probes, catheters, endoscopes, capsules, and needles (e.g., a biopsy needle).

BACKGROUND OF THE DISCLOSURE

Percutaneous coronary intervention (PCI) has improved since the introduction of intravascular imaging (IVI) modalities such as intravascular ultrasound (IVUS) and optical coherence tomography (OCT). IVI modalities provide cross-sectional imaging of coronary arteries with precise lesion information, (e.g., lumen size, plaque morphology, and implanted devices).

However, only about 20% of interventional cardiologists in the United States use IVI imaging with or without coronary angiography during PCI procedures. Typical IVI IVUS and OCT systems provide a 10 mm imaging field of view (FOV) so as to be able to image vessels as large as 3.5 mm to 4.0 mm in diameter, due to factors such as catheter eccentricity, oblique beam illumination, and the desire to visualize tissue to a depth of at least 1.0 mm to 1.5 mm. A good percentage of vessels however, especially ones with stenosis, are as small as 1.5 mm to 2.5 mm. Accordingly only a small portion of the imaging FOV is available for the actual object of interest, rendering the imaged object very small and hard to visualize. Furthermore, it is worth noting that one of the reasons why IVUS and OCT are not commonly used in PCI is that it is difficult for interventional cardiologists to interpret the acquired IVUS and OCT images, due to lack of clarity, inconsistencies while retracting the OCT, and general imaging issues.

Intraluminal cross-sectional images have the potential to be displayed with high detail. However, it is hard to choose a field of view that has the right magnification level about the imaged object throughout the full pullback due to the fact that most luminal organs vary in size along the pullback direction and that the probe is usually eccentric within the lumen. FIG. 1a shows a cross-sectional image acquired with OCT of a right coronary ascending (RCA) vessel with a 3.5 mm mean lumen diameter displayed with the system's imaging FOV of 10 mm. Although the vessel is large, the object of interest, the lumen and underlying tissue structure, covers only a portion of the image. FIG. 1b is a magnified version of the same cross-sectional image displayed in FIG. 1a, at the 7.0 mm FOV magnification level. FIG. 1b utilizes the standard magnification technique as currently taught in the art and appears to work just fine since the center of the image FOV is about the same as the center of the imaged object's lumen. In other words, since catheter eccentricity with the vessel lumen is minimal, the catheter is almost centered with the vessel lumen, providing centered magnification of the original image.

However, as can be seen from FIG. 2, the catheter and the lumen are eccentric with respect to one another, and the catheter is situated closer to the lumen surface. The imaged object is the same as the one in FIG. 1a, although the image is acquired during a different pullback but with the same catheter and system, albeit with a slightly different detection scheme that bears no effect for comparison purposes. Similar to FIG. 1b, FIG. 3 is a magnified version of the same cross-sectional image of FIG. 2, displayed at the 7.0 mm FOV magnification level using the standard magnification technique. As can be seen the current technique does not work well when the catheter is not centered in the lumen. As important structural tissue information is lost in the fourth quadrant of the image (lower right side) due to the center of the image FOV being very different from the center of the imaged object's lumen. This misaligned imaging is due to catheter eccentricity within the vessel lumen, wherein the catheter is closer to one side of the vessel lumen.

Accordingly, it is particularly beneficial to devise methods and systems for displaying real-time images of a lumen with high accuracy at a high magnification level. And even more so, to devise methods and systems for displaying real-time images of a lumen with high accuracy while the imaging apparatus is being advanced and/or retracted through the lumen.

SUMMARY

Thus, to address such exemplary needs in the industry, the presently disclosed apparatus teaches a system for manipulating an image captured by a medical device, the system employing: a processor; a memory coupled to the processor, the memory having instructions for manipulating the image, the instructions comprising: receiving data corresponding to the image; detecting a feature within the image; determining the center of the image based on the feature; and adjusting the image based on the determined center of the image.

In various embodiments, the subject disclosure may further comprise magnifying the image, which may be accomplished at nearly any point of the system. In addition, the degree of the magnifying of the image may be calculated based on the detected feature, so as to ensure adequate or maximum magnification, without losing any pertinent details.

In various embodiments, the feature detected may be an outer edge of a facet on the captured image. By way of example, the facet may be a cavity, signal containing tissue, or other similar markers and/or structures in the image.

In yet additional embodiments of the disclosure, the feature detected may be an outer periphery of the facet.

Further embodiment of the subject disclosure contemplate the acquisition of data, corresponding with the image, to be acquired by optical coherence tomography, intravenous ultrasound imaging, alternatives thereof and combinations therefrom.

In yet additional embodiments, the processor may perform polar to Cartesian transformation of the image to assist in imaging.

In other embodiments, the subject disclosure further comprises interpolating a circumscribed area of the image.

In yet other embodiment, the subject disclosure teaches using multiple images captured by a medical device for processing by the processor, thus creating a continuous motion picture.

The subject disclosure also teaches a computer-based method for manipulating an image which may be captured by a medical device, the method comprising the steps of: receiving data corresponding to the image; detecting a feature within the image; determining the center of the image based on the feature; and adjusting the image based on the determined center of the image.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

FIGS. 1a and 1b depict cross-section images of a lumen using a catheter mostly centered in the vessel lumen, according to existing imaging methods, wherein FIG. 1b is a magnification of FIG. 1a.

Figure 1A:
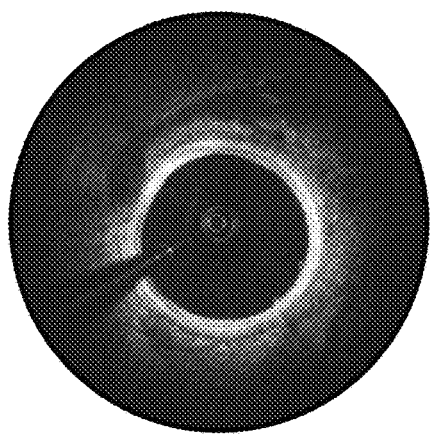
Figure 1B:
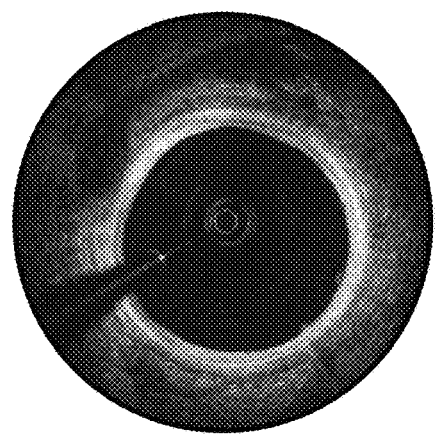

Throughout the Figures, the same reference numerals and characters, unless otherwise stated, are used to denote like features, elements, components or portions of the illustrated embodiments. In addition, reference numeral(s) including by the designation "'" (e.g. 12' or 24') signify secondary elements and/or references of the same nature and/or kind. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION OF THE DISCLOSURE

Figure 2:
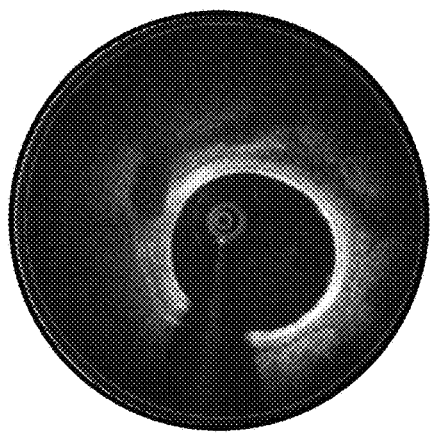
FIG. 2 depicts a cross-section image of a lumen using a catheter mostly eccentric in the vessel lumen, according to existing imaging methods.
Figure 3:
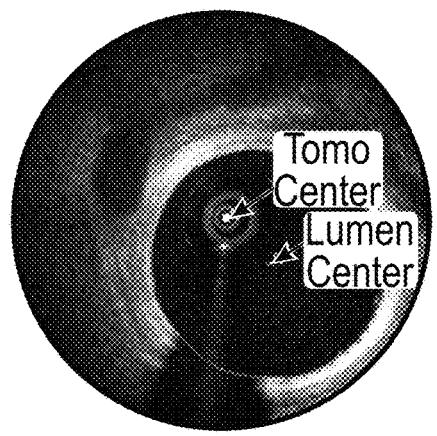
FIG. 3 is a magnification of FIG. 2, according to one or more embodiment of the subject apparatus, method or system.
Figure 4:
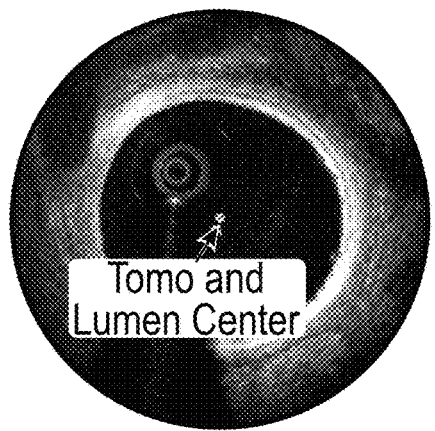
FIG. 4 depict the same image of the lumen provided in FIG. 3, incorporating the subject optimization, according to one or more embodiment of the subject apparatus, method or system.

FIG. 3 is a magnified version of the same porcine OCT cross-sectional image provided in FIG. 2, wherein details regarding the detected lumen edge outline and indication of the lumen center as calculated from the detected lumen edge are provided. As can be seen from FIG. 3, using existing magnification techniques, the center of the image FOV deviates greatly from the center of the imaged lumen. This deviation is due to catheter eccentricity within the vessel, which causes the image to not be centered. As such, important structural tissue information is lost in the fourth quadrant (lower left-hand side) of the image. FIG. 4, on the other hand, shows the same cross-sectional image as that of FIG. 3 at the same magnification level, and is provided for comparison purposes. As one can see, by applying the subject optimized magnification, no structural tissue information is lost throughout the imaged object, and the image is centered. When compared to the standardized optimization technique provided in FIG. 3, FIG. 4 provided a complete image of the lumen, allowing for more thorough and compelling analysis.

Figure 5:
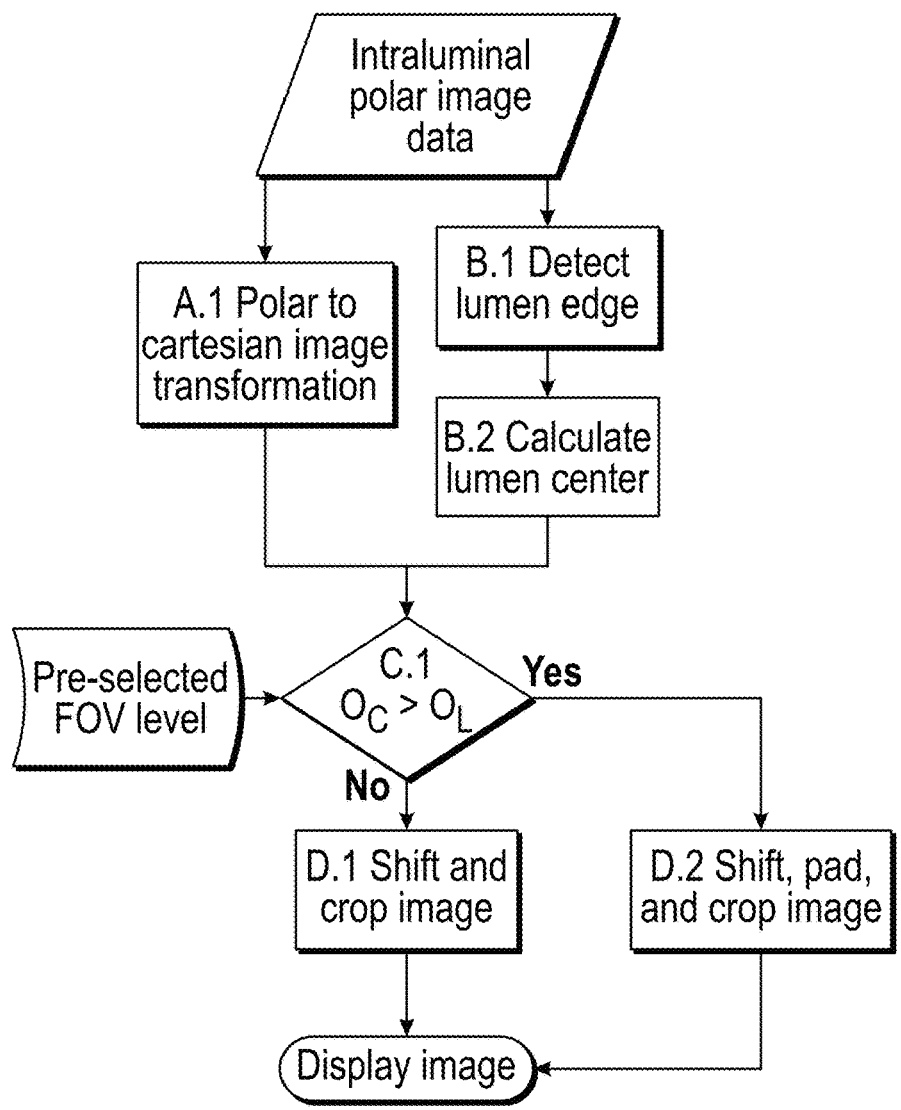
FIG. 5 provides an exemplary flowchart, according to one or more embodiment of the subject apparatus, method or system.

FIG. 5 is a flowchart describing the steps taken to implement a first embodiment of the subject disclosure. Once intraluminal image data is available, a processing unit calculates steps A and B, which can be performed serially or in parallel. Step A.1 performs Polar to Cartesian transformation of the image data. Several methods can be used, including spline, linear, or any other interpolation method. Step B.1 performs lumen edge detection on the polar data, for which many algorithms can be implemented. For efficiency, if need be, a subset of A-lines can be used (e.g. every $10^{th}$ A-line) but if computation is not a concern or if the lumen has to be calculated anyway for other purposes like lumen measurement or calibration of NIRAF data, in the case of a second modality like MMOCT (OCT and NIRAF), then all A-lines can be used which can be more accurate. Step B.2 calculates lumen edge center x- and y-coordinates, Cc (x, y), by transforming lumen edge for detected A-lines to Cartesian coordinates, then summing along the x- and y-coordinates, and dividing by the number of detected lumen edges to obtain Cc (x, y). Arithmetic median, mean, mode, and other metrics can be used to determine lumen center. Step C.1 compares for all A-lines calculated offset between calculated lumen center and tomographic image center, $O_C$ (x, y), and crop amount, $O_L$, where $O_L$ is given by equation 1.

$$O_L=(N_{PX}/2)*(FOV_F-FOV_L)/FOV_F \qquad \text{Eq. 1}$$

$N_{PX}$ is the number of pixels per A-line; $FOV_F$ is the full, original image FOV before any magnification; $FOV_L$ is the desired FOV level. If $O_L$ is greater than $O_C$ for the whole image. This is followed by Step D.1, where shift Cartesian image data by $O_C$ (x, y) and crop $O_L$ pixels from beginning and end of the data. If $O_L$ is smaller than $O_C$ for a subset of the image then, Step D.2, shift polar image data by $O_C$ (x, y) and pad the subset of the image with background data then crop $O_L$ pixels from beginning and end of the data. The cropping and padding order can be interchanged. Black pixel data can be inserted instead of background data. Image data can then be displayed.

Figure 6:
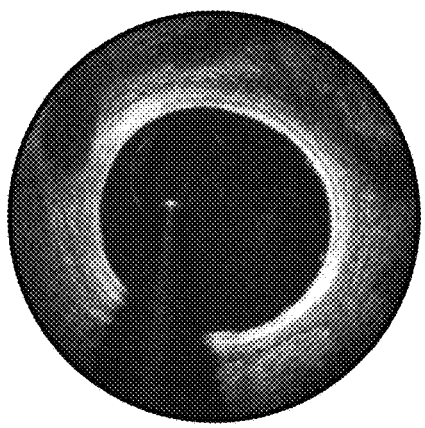
FIG. 6 is cross-section image of a lumen, according to one or more embodiment of the subject apparatus, method or system.

In a further embodiment, the catheter sheath outside diameter may be detected and the circumscribed area pixels are interpolated with background data values so as to remove the catheter from the image. With varying catheter eccentricity levels within the lumen, the location of the catheter in the image can vary substantially, distracting the physician from important features. Ideally the background data is copied from the signal-free or signal-weak regions within the lumen so as to maintain similar texture and speckle pattern. FIG. 6 shows the same cross-sectional image as that of FIG. 4, at the same magnification level, without lumen overlay and with values of the pixels circumscribed by the catheter sheath outer layer interpolated by background data from the signal-free region of the lumen.

Figure 7:
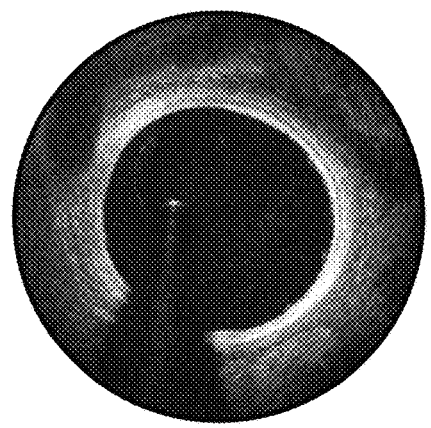
FIG. 7 illustrates a cross-section image of a lumen, according to one or more embodiment of the subject apparatus, method or system.

A second embodiment of this disclosure describes the steps needed to magnify the image to a pre-specified magnification level. FIG. 7 shows the results of said optimized magnification to a 7 mm pre-selected FOV level down from the initial 10 mm FOV, which corresponds to a 2× magnification level, with potential for improved resolution compared to the first embodiment.

Figure 8:
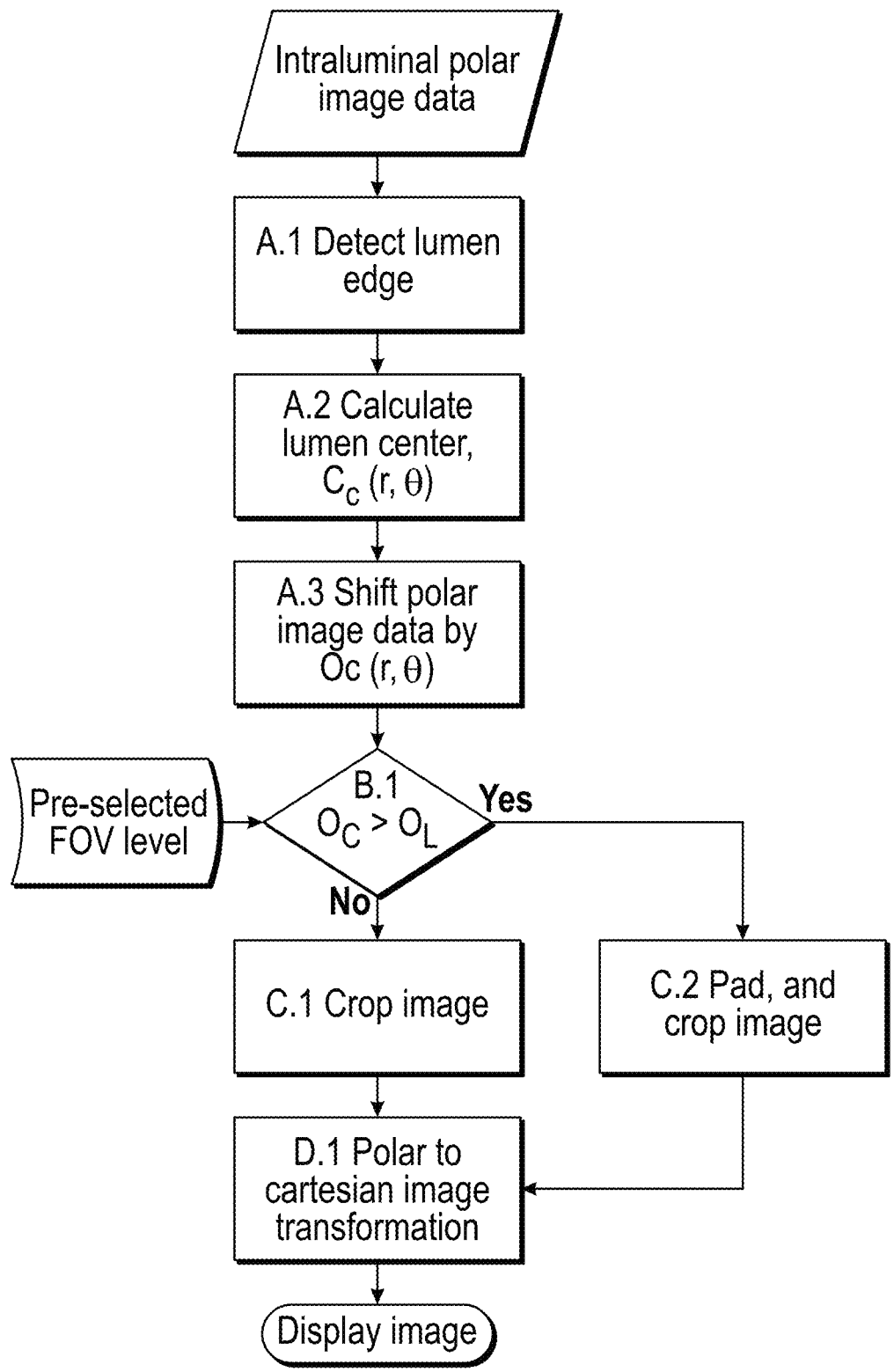
FIG. 8 provides an exemplary flowchart, according to one or more embodiment of the subject apparatus, method or system.

FIG. 8 is a flowchart describing the steps taken to implement the second embodiment. Step A.1 detects lumen edge from polar image data. Step A.2 calculates lumen center r- and θ-coordinates, Cc (r, θ), by transforming lumen edge for detected A-lines from polar to Cartesian coordinates then summing along the x-, and y-coordinates and dividing by the number of detected lumen edges, then converting to polar coordinates to obtain Cc (r, θ). Step A.3 shifts polar image data by the calculated offset between calculated lumen center and tomographic image center, $O_C$ (r, θ). Step B.1 compares for all A-lines calculated offset between calculated lumen center and tomographic image center, $O_C$ (r, θ). If $O_L$ is greater than $O_C$ for the whole image, then Step C.1, crop $O_L$ pixels from beginning and end of the data. If $O_L$ is smaller than $O_C$ for a subset of the image, then Step C.2, pad the subset of the image with background data then crop $O_L$ pixels from beginning and end of the data. Step D.1 performs Polar to Cartesian transformation of the image data.

Polar to Cartesian scan conversion usually involves under-sampling, therefore limiting or reducing the original image resolution. (E.g. a polar image that is 500 A-lines by 1024 pixels per depth profile or A-line, is transformed to a 1024 by 1024 Cartesian, cross-sectional image which corresponds to two depth profiles). Pixels in the center of the cross-sectional image get compressed but pixels in the outer edges of the cross-sectional image get stretched. And the 2048 pixels for two depth profiles are represented as 1024 pixels only, or a factor of 2 down-sampling. A reduction, therefore, of FOV (i.e. image magnification) which includes cropping of the original data before scan conversion can only limit the effect of under-sampling. For example a reduction of FOV from 10 mm to 7 mm leads to an improvement of 1.4 in sampling density both radially and laterally, or a similar value of resolution improvement for systems that are sampling limited and not native resolution limited.

Figure 10A:
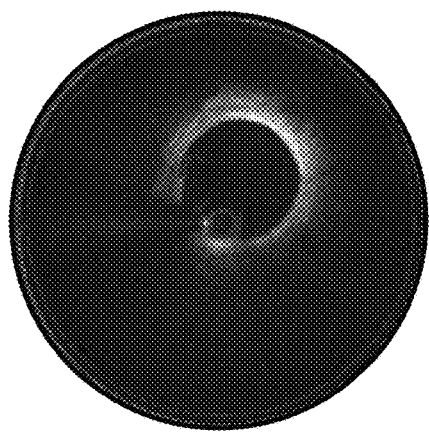
FIG. 10a-10c depict cross-section image of a lumen, wherein 10a has no magnification, and 10b and 10c incorporate the subject optimization, according to one or more embodiment of the subject apparatus, method or system.
Figure 10B:
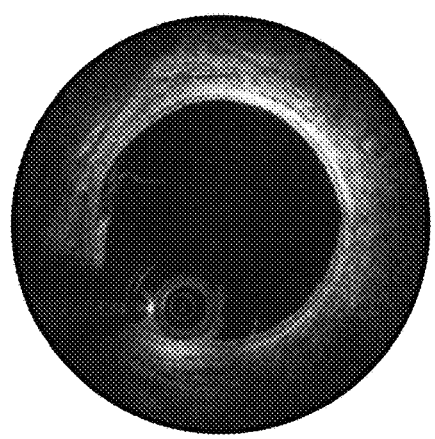
Figure 10C:
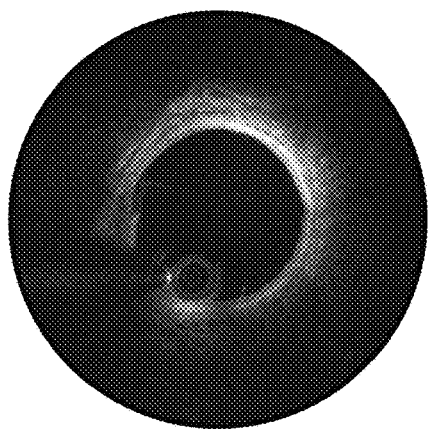
Figure 11A:
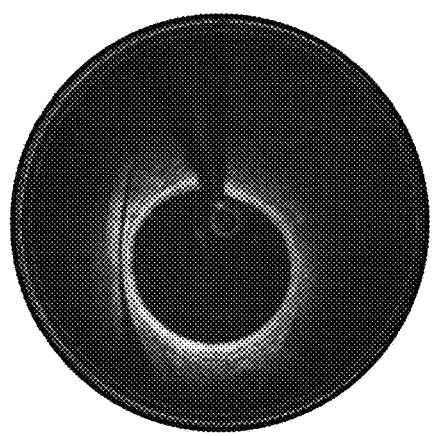
FIG. 11a-11c depict cross-section image of a lumen, wherein 11a has no magnification, and 11b and 11c incorporate the subject optimization, according to one or more embodiment of the subject apparatus, method or system.
Figure 11B:
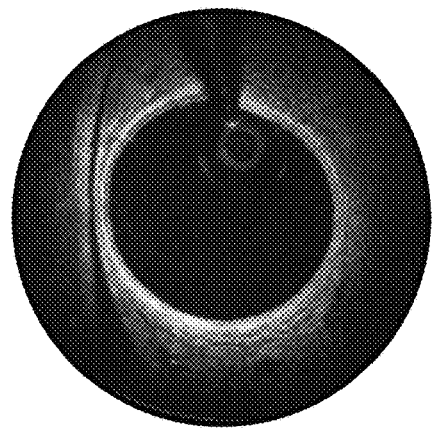
Figure 11C:
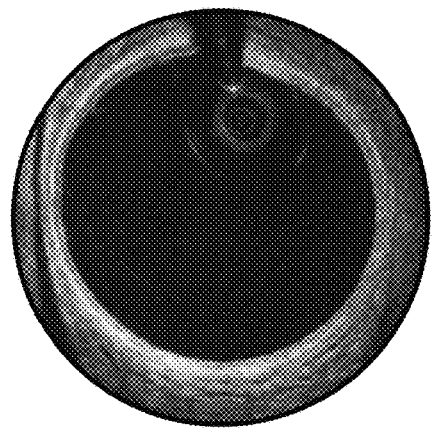

The third embodiment of this disclosure describes the steps needed to adaptively magnify the image to a level that focuses on the imaged object as much as possible without cropping key imaged object features. FIG. 10a shows a distal cross-sectional image of a porcine LAD vessel, 2.7 mm in diameter. FIG. 11a shows a proximal cross-sectional image of the same porcine LAD vessel, 3.6 mm in diameter, acquired during the same pullback recording. FIG. 10b is the result of the adaptive optimized magnification process for the distal LAD image and, as can be seen, the imaged object is centered and prominent in the image. The adaptive magnification level adjusted the FOV to 5 mm (4× magnification). If a pre-selected 7 mm FOV (about 2× magnification) level was chosen for the whole pullback, then the object image, although centered, is not very prominent in the image as can be seen from FIG. 10c. FIG. 11b is the result of the adaptive optimized magnification process for the proximal LAD image and, as can be seen, the imaged object is centered and prominent in the image. The adaptive magnification level adjusted the FOV to 7 mm (about 2× magnification). If a pre-selected 5 mm FOV (4× magnification) level was chosen for the whole pullback then the object image, although centered, is cropped at the edges and key features can be missing as can be seen from FIG. 11c.

A single fixed optimized magnification level, although better than standard magnification, is therefore not necessarily optimized for a whole pullback recording where the imaged object size varies substantially.

Figure 9:
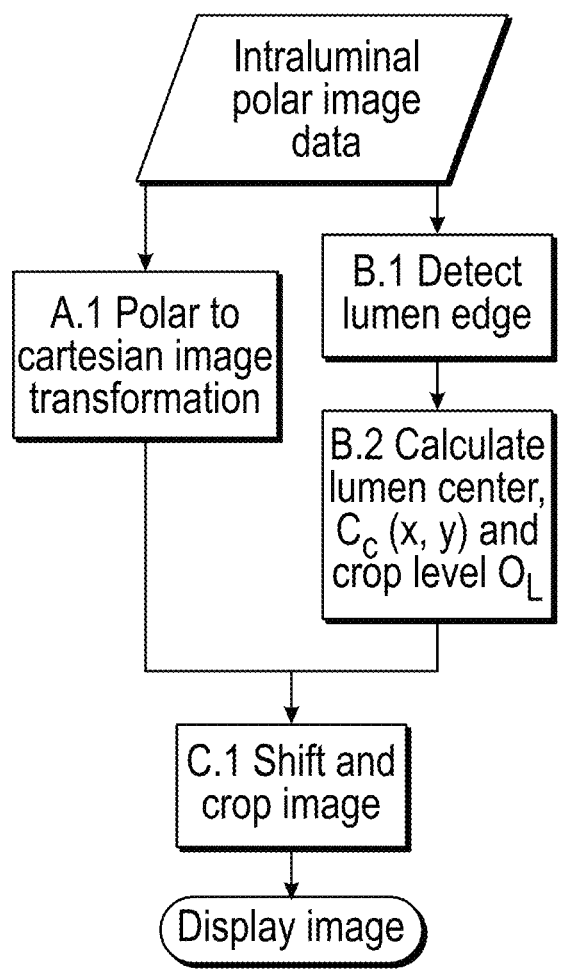
FIG. 9 provides an exemplary flowchart, according to one or more embodiment of the subject apparatus, method or system.

FIG. 9 is a flowchart describing the steps taken to implement embodiment 3. Step A.1 performs Polar to Cartesian transformation of the image data. Step B.1 performs lumen edge detection on the polar data. Step B.2 calculates lumen edge center x- and y-coordinates, Cc (x, y), by transforming lumen edge for detected A-lines to Cartesian coordinates, then summing along the x- and y-coordinates, and dividing by the number of detected lumen edges to obtain Cc (x, y), and then determines crop amount, $O_L$, where $O_L$ is given by equation 2.

$$O_L=(N_{PX}/2)*(P_D/FOV_F) \qquad \text{Eq. 2}$$

$N_{PX}$ is the number of pixels per A-line; $FOV_F$ is the full, original image FOV before any magnification; $P_D$ is the tissue penetration depth. $P_D$ can be a fixed pre-selected value for example 1 mm, or it can be measured from the image data itself as the max, mean, or median tissue depth measured from the lumen. The tissue depth can be determined as the depth at which the signal drops to the noise floor or an offset from the noise floor for example. Step C.1 shifts polar image data by $O_C$ (x, y) then crops $O_L$ pixels from beginning and end of the data. Cropping and padding order can be reversed. Image data can then be displayed.

The fourth embodiment is similar to the third embodiment in such a way that the resultant images are very similar to FIGS. 10b and 11b. The only difference is in the processing steps.

Figure 12:
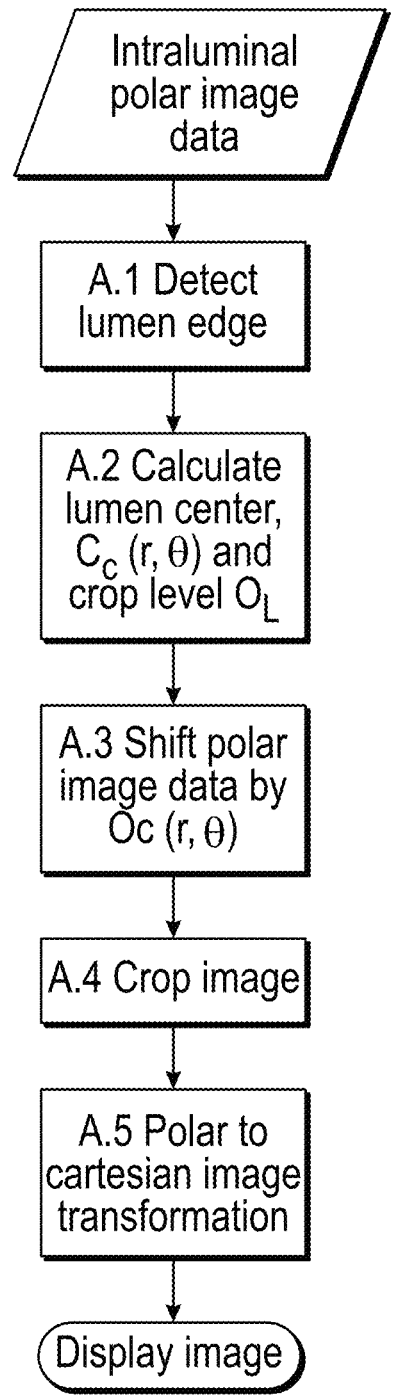
FIG. 12 provides an exemplary flowchart, according to one or more embodiment of the subject apparatus, method or system.

FIG. 12 is a flowchart describing the steps taken to implement embodiment 4. Step A.1 detects the lumen edge from polar image data. Step A.2 calculates lumen center r- and θ-coordinates, Cc (r, θ), by transforming lumen edge for detected A-lines from polar to Cartesian coordinates, then summing along the x- and y-coordinates and dividing by the number of detected lumen edges, then converting to polar coordinates to obtain Cc (r, θ), and then determines crop amount, $O_L$, where $O_L$ is given by equation 2. Step A.3 shifts polar image data by the calculated offset between calculated lumen center and tomographic image center, $O_C$ (r, θ). Step A.4 crops $O_L$ pixels from beginning and end of the data. Step A.5 performs Polar to Cartesian transformation of the image data, thereafter, the image data can then be displayed.

Figure 13A:
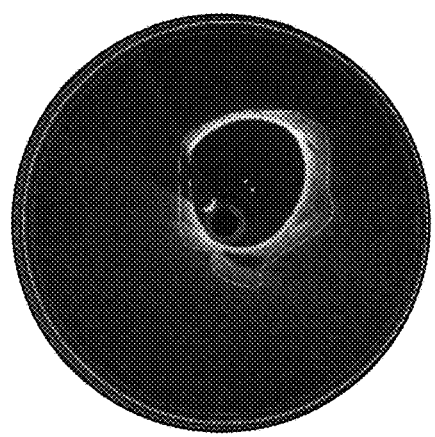
FIG. 13a-13c depict cross-section image of a lumen, wherein 11a has no magnification, 11b incorporates magnification centered upon the lumen, and 11c incorporate magnification centered upon the edge of a signal containing issue, according to one or more embodiment of the subject apparatus, method or system. In various other embodiments, the image centering may be controlled by a user, wherein the user may determine what the center of the image should be. This may be implemented before or after magnification.
Figure 13B:
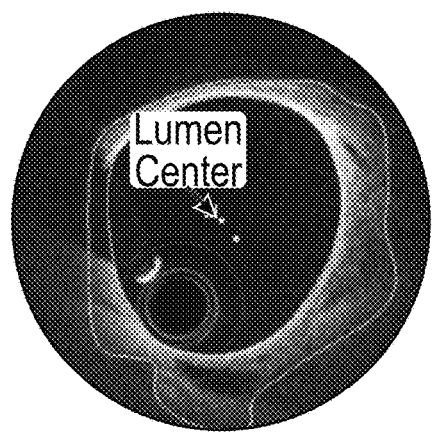
Figure 13C:
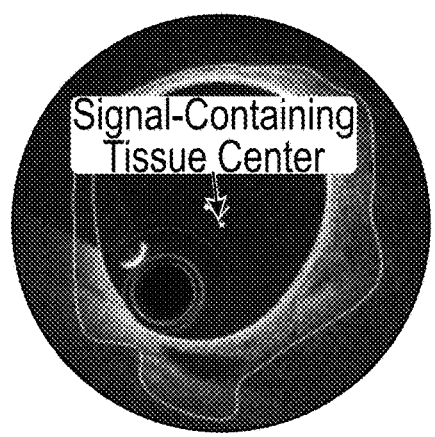

The fifth to eight embodiments are similar to the first to fourth embodiments, respectively, except that instead of using the lumen center as the center of the tomographic image, the system can use the center of the vessel wall, or the external elastic lamina, or the edge of the signal containing tissue. FIG. 13a shows a cross-sectional image of a porcine vessel, 2.6 mm in diameter at full FOV (no magnification). FIG. 13b shows a cross-sectional image of the same porcine vessel, 2.6 mm in diameter 5 mm FOV (4× magnification), where the image is shifted such that the center of the image is the center of the lumen as is the case in embodiments 1 to 4. FIG. 13c shows a cross-sectional image of the same porcine vessel, 2.6 mm in diameter 5 mm FOV (4× magnification), where the image is shifted such that the center of the image is the center of the edge that circumvents the signal-containing tissue.

The ninth embodiment is an extension of any of the previous embodiment wherein the optimally magnified tomographic data is used to reconstruct longitudinal view, 3D view, splayed view, carpet view, etc. This optimized magnification process has the added advantage of making variations in longitudinal cut smaller, less pronounced, that when the cut is not through the vessel center but the catheter center. It also allows for better visualization of key features since the image is optimally magnified about the imaged object.

Processing can be run in real time with un-noticeable or minimal image processing and display latency, using optimized algorithms and powerful central processing units, graphic processing units, tensor processing units, field programmable gated arrays, and other purpose specific processing units.

The tenth embodiment is an extension of the previous embodiments wherein the methods of centering takes into consideration gaps in data, due to, for example, guide wires or stents, by either ignoring those data points or interpolating between valid points. Also taken into consideration are side branches where the edge for the side branches is, in one example, detected in addition to the main vessel edge for making the center point calculation and ignored in another, leading to a gap in the data that is treated similarly to a guide wire or stent.

While the present disclosure has been described with reference to exemplary embodiments, it is to be understood that the disclosure is not limited to the subject exemplary embodiments. The scope of the following claims is to be accorded the broadest interpretation so as to encompass all such modifications and equivalent structures and functions.

The invention claimed is:

1. A system for manipulating an image captured by a medical device, the system employing:
    a processor;
    a memory coupled to the processor, the memory having instructions for manipulating the image, the instructions comprising:
    receiving data corresponding to the image;
    detecting a feature within the image;
    determining the center of a lumen within the image based on the feature;
    adjusting the image based on a size of the lumen and the determined center of the lumen within the image; and
    magnifying the image such that the magnified image displays a centered field of view, wherein the centered field of view is determined based on the size of the lumen and center of the lumen.

2. The system of claim 1, wherein a degree of the magnifying of the image is calculated based on the detected feature.

3. The system of claim 1, wherein the detected feature is an outer edge of a facet on the image.

4. The system of claim 3, wherein the facet is a cavity.

5. The system of claim 3, wherein the facet is a signal containing tissue.

6. The system of claim 3, wherein the detected feature is an outer periphery of the facet.

7. The system of claim 1, wherein the data corresponding with the image is acquired by optical coherence tomography.

8. The system of claim 1, wherein the data corresponding with the image is acquired by intravenous ultrasound imaging.

9. The system of claim 1, wherein the processor performs polar to Cartesian transformation of the image.

10. The system of claim 1, further comprising interpolating a circumscribed area of the image.

11. The system of claim 1, further comprising multiple images captured by the medical device for processing by the processor, creating a continuous motion picture.

12. The system of claim 1, wherein the adjusting the image based on the determined center of the image is manually adjusted by an end user.

13. The system of claim 1, wherein magnifying the image is continually adjusted as the size of the lumen changes during a pullback procedure.

14. A computer-based method for manipulating an image which may be captured by a medical device, the method comprising the steps of:
    receiving data corresponding to the image;
    detecting a feature within the image;
    determining the center of a lumen within the image based on the feature;
    adjusting the image based on a size of the lumen and the determined center of the lumen within the image; and
    magnifying the image such that the magnified image displays a centered field of view, wherein the centered field of view is determined based on the size of the lumen and center of the lumen.

15. The method of claim 13, wherein a degree of the magnifying of the image is calculated based on the detected feature.

16. The method of claim 13, wherein the detected feature is an outer edge of a facet on the image.

17. The method of claim 16, wherein the facet is a cavity.

18. The method of claim 16, wherein the facet is a signal containing tissue.

19. The method of claim 16, wherein the detected feature is an outer periphery of the cavity.

20. The method of claim 13, wherein magnifying the image is continually adjusted as the size of the lumen changes during a pullback procedure.

* * * * *